(12) United States Patent
Georgeson et al.

(10) Patent No.: US 10,502,697 B2
(45) Date of Patent: Dec. 10, 2019

(54) HIGH SPEED PIPE INSPECTION SYSTEM

(71) Applicant: The Boeing Company, Chicago, IL (US)

(72) Inventors: Gary Ernest Georgeson, Tacoma, WA (US); Morteza Safai, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 241 days.

(21) Appl. No.: 15/701,301

(22) Filed: Sep. 11, 2017

(65) Prior Publication Data

US 2019/0079028 A1 Mar. 14, 2019

(51) Int. Cl.
*G01N 23/02* (2006.01)
*G01N 23/203* (2006.01)
(Continued)

(52) U.S. Cl.
CPC .............. *G01N 23/02* (2013.01); *G01N 23/18* (2013.01); *G01N 23/203* (2013.01); *G01N 23/046* (2013.01); *G01N 2223/308* (2013.01); *G01N 2223/32* (2013.01); *G01N 2223/3301* (2013.01); *G01N 2223/3303* (2013.01); *G01N 2223/3308* (2013.01); *G01N 2223/601* (2013.01);
(Continued)

(58) Field of Classification Search
CPC ...... G01N 23/02; G01N 23/18; G01N 23/203; G01N 2223/3303; G01N 23/046; G01N 2223/629; G01N 2223/601; G01N 2223/32; G01N 2223/66; G01N 2223/308; G01N 2223/646; G01N 2223/628; G01N 2223/3301; G01N 2223/3308
See application file for complete search history.

(56) References Cited

U.S. PATENT DOCUMENTS

| 5,007,291 A | 4/1991 | Walters et al. |
| 5,420,427 A * | 5/1995 | Morgan ................. G01N 23/18 |
| | | 250/358.1 |

(Continued)

FOREIGN PATENT DOCUMENTS

| DE | 4302286 C1 | 6/1994 |
| GB | 2211708 A | 7/1989 |

(Continued)

OTHER PUBLICATIONS

European Patent Office Extended Search Report, dated Feb. 28, 2019, regarding Application No. 18190337.8, 9 pages.
(Continued)

*Primary Examiner* — Michael C Bryant
(74) *Attorney, Agent, or Firm* — Yee & Associates, P.C.

(57) ABSTRACT

A method, apparatus, and system for scanning an elongate structure. A scanner in a scanning system is moved axially along the elongate structure using a translating structure in the scanning system. The elongate structure is scanned axially using an x-ray beam emitted by the scanner as the scanner moves axially along the elongate structure to perform an axial scan. The x-ray beam has a first orientation. A location on the elongate structure having an inconsistency is detected while scanning the elongate structure axially. The elongate structure is scanned at the location with the x-ray beam in a second orientation.

28 Claims, 11 Drawing Sheets

(51) Int. Cl.
    *G01N 23/18*         (2018.01)
    *G01N 23/046*        (2018.01)
(52) U.S. Cl.
    CPC . *G01N 2223/628* (2013.01); *G01N 2223/629* (2013.01); *G01N 2223/646* (2013.01); *G01N 2223/66* (2013.01)

(56) References Cited

U.S. PATENT DOCUMENTS

| | | | |
|---|---|---|---|
| 6,106,152 | A | 8/2000 | Thunberg |
| 8,759,780 | B2 | 6/2014 | Dobbs |
| 9,709,514 | B2 | 7/2017 | Edwards et al. |
| 2005/0041775 | A1* | 2/2005 | Batzinger ............ G01N 23/04 378/59 |
| 2011/0168900 | A1* | 7/2011 | Dobbs .................. G01B 15/02 250/360.1 |

FOREIGN PATENT DOCUMENTS

| | | |
|---|---|---|
| RU | 2496106 C1 | 10/2013 |
| WO | WO2011023960 A1 | 3/2011 |
| WO | WO2011045563 A1 | 4/2011 |
| WO | WO2015138329 A1 | 9/2015 |
| WO | WO2015166266 A1 | 11/2015 |

OTHER PUBLICATIONS

European Patent Office Extended Search Report, dated Mar. 8, 2019, regarding Application No. 18190331.1, 7 pages.

"Twomey, "Inspection Techniques for Detecting Corrosion Under Insulation," Inspectioneering Journal Nov./Dec. 1996, accessed Aug. 8, 2017, 6 pages. https://inspectioneering.com/journal/1996-11-01/116/inspection-techniques-for-dete".

Safai et al., "X-Ray Inspection System for Pipes," U.S. Appl. No. 15/701,244, filed Sep. 11, 2017, 44 pages.

* cited by examiner

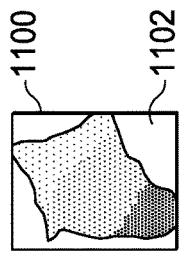
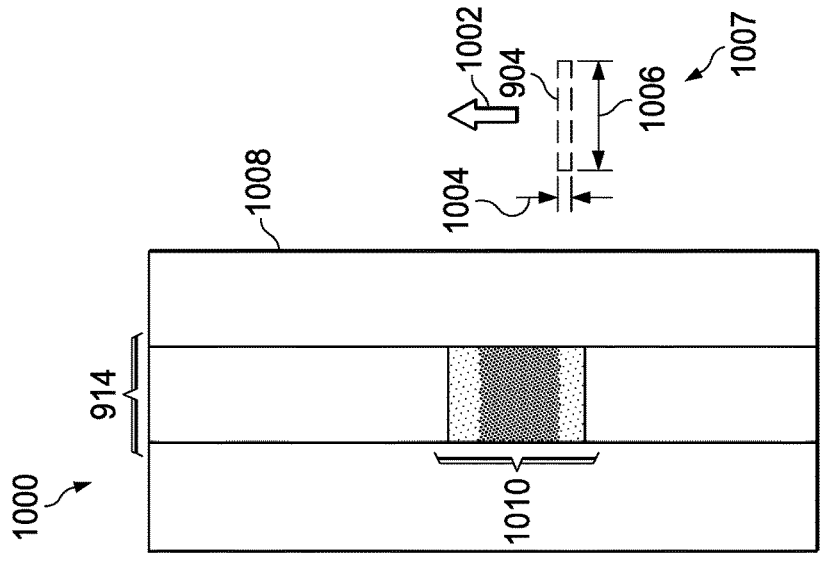
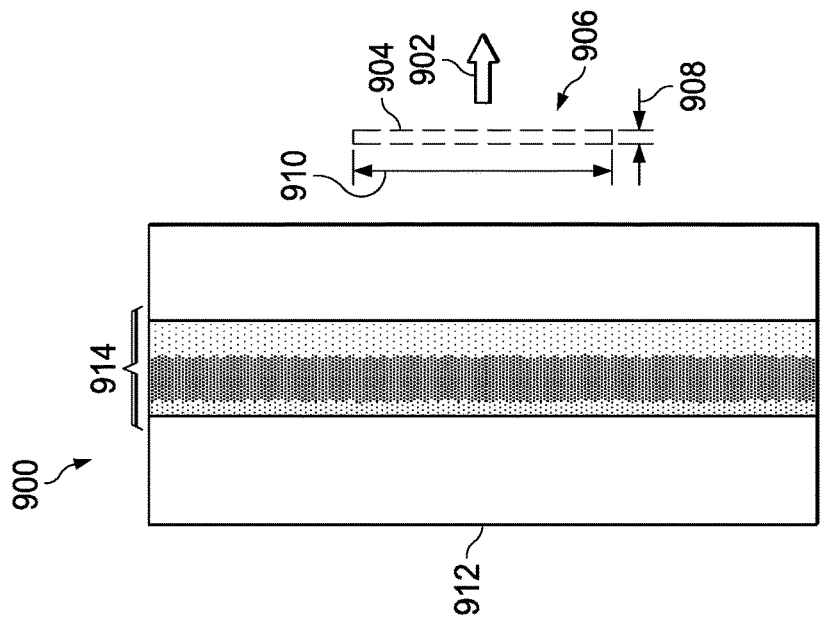

HIGH SPEED PIPE INSPECTION SYSTEM

CROSS-REFERENCE TO RELATED APPLICATION

This application is related to U.S. Patent Application entitled "X-Ray Inspection System for Pipes," Ser. No. 15/701,244, filed even date hereof, and incorporated herein by reference in its entirety.

BACKGROUND INFORMATION

1. Field

The present disclosure relates generally to inspection systems and, in particular, to nondestructive inspection of elongate structures. Still more particularly, the present disclosure relates to a method, apparatus, and system for nondestructive inspection of insulated pipes using x-ray scanners.

2. Background

Pipes are used in many industries to transport fluids. For example, the oil and gas industry uses pipes to transport oil and gas. Pipes for transporting oil are made from steel or plastic and are usually buried. The oil is moved through the pipes by pump stations along the pipeline.

Natural gas and similar gas fuels are pressurized into liquid form. Natural gas pipes are often constructed of carbon steel. As another example, district heating or teleheating systems use a network of insulated pipes which transport heated water, pressurized hot water, or sometimes steam, to the customer.

Water supply systems also employ pipes to transport drinking water to customers. Pumps pressurize potable water that flows through pipes to deliver water for consumption.

Pipe inspections are performed to determine the condition of the pipes. For example, an inspection may be made to determine whether obstructions, corrosion, or other inconsistencies are present in the pipes. Inspections also may be performed to determine wall thickness, weld quality, as well as other parameters. The pipe inspections involve nondestructive testing and may be performed in a number of different ways. For example, pipe inspections may be made using video. This type of inspection, however, involves introducing a device into the pipes. Another type of inspection uses x-rays. This type of testing allows for the inspection to be made from the exterior of the pipe.

One manner in which current x-ray inspections are performed is by hand. A human operator moves an x-ray scanning system along the pipe to perform the inspection. With insulated pipes, x-rays are directed through the pipe from a source on one side of the pipe and detected by a detector on the opposite side of the pipe to generate an image. In many cases, with insulated pipes, the source is then moved to the other side of the pipe and another image is generated.

A pipe for transporting oil may extend for hundreds of miles. Inspecting hundreds of miles of pipe is a time-consuming and tedious process using current techniques. Further, identifying corrosion under insulation (CUI) is often more difficult than desired. Corrosion occurring under insulation may be difficult to identify because an insulation covering the pipe may mask the corrosion. Removing the insulation for inspection to check the surface condition of a pipe and replacing the insulation is undesirable because of the cost and time lost.

Profile radiography is a technique that may be used to inspect insulated pipes. X-rays are sent through a small section of pipe wall. A comparator block is also included in the transmission which is used to calculate the wall thickness of the pipe. This type of technique is useful, but often becomes challenging in a pipe system having pipes over ten inches in diameter.

Further, scanning a long length of pipe may be less efficient than desired. Pipeline systems may have pipes that extend for hundreds of miles. For example, inspecting the pipes using x-ray scans is time consuming and expensive.

Therefore, it would be desirable to have a method and apparatus that take into account at least some of the issues discussed above, as well as other possible issues. For example, it would be desirable to have a method and apparatus that overcome a technical problem with scanning an insulated pipe for inconsistencies with a desired level of efficiency.

SUMMARY

An embodiment of the present disclosure provides a scanning system. The scanning system comprises of a translating structure, a scanner, and a controller. The translating structure is configured to move axially along an elongate structure. The scanner is connected to the translating structure. The scanner is configured to scan the elongate structure utilizing an x-ray beam configured to have a first orientation and a second orientation substantially perpendicular to the first orientation. The controller is in communication with the translating structure and the scanner. The controller controls the translating structure to move axially along the elongate structure while the scanner performs an axial scan of the elongate structure using the x-ray beam at the first orientation. The scanner performs a second scan of the elongate structure using the x-ray beam at the second orientation when an inconsistency is detected in the axial scan at a location on the elongate structure.

Another embodiment of the present disclosure provides a pipe scanning system. The pipe scanning system comprises of a translating structure, a scanner, and a controller. The translating structure is configured to move axially and rotationally on a pipe. The scanner is connected to the translating structure. The scanner is configured to scan an object utilizing an x-ray beam configured to have a first orientation and a second orientation that is substantially perpendicular to the first orientation. The controller is in communication with the translating structure and the scanner. The controller controls the translating structure to move axially along the pipe while the scanner performs an axial scan of the pipe using the x-ray beam at the first orientation and move rotationally to perform a rotational scan of the pipe using the x-ray beam at the second orientation when an inconsistency is detected in the axial scan at a location on the pipe. The controller combines first data from the axial scan at the location with second data from the rotational scan at the location to form an image of the inconsistency at the location.

Yet another embodiment of the present disclosure provides a method for scanning an elongate structure. A scanner in a scanning system is moved axially along the elongate structure using a translating structure in the scanning system. The elongate structure is scanned axially using an x-ray beam emitted by the scanner as the scanner moves axially along the elongate structure to perform an axial scan. The x-ray beam has a first orientation. A location on the elongate structure having an inconsistency is detected while scanning the elongate structure axially. The elongate structure is scanned at the location with the x-ray beam in a second orientation.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 9 is an illustration of an axial scan in accordance with an illustrative embodiment;

FIG. 10 is an illustration of a second scan in accordance with an illustrative embodiment;

FIG. 11 is an illustration of an image generated from an axial scan and a second scan of a pipe in accordance with an illustrative embodiment;

DETAILED DESCRIPTION

The illustrative embodiments recognize and take into account one or more different considerations. For example, the illustrative embodiments recognize and take into account that scanning an elongate structure, such as a pipe, involves obtaining a sufficient amount of data about the pipe to identify inconsistencies that may be present. The illustrative embodiments recognize and take into account that obtaining the desired amount of data along the length of the pipe to identify inconsistencies is less efficient than desired. For example, the illustrative embodiments recognize and take into account that scanning the length of a pipe to generate images with a sufficient resolution to identify and characterize inconsistencies in the pipe may take more time than desired.

Thus, the illustrative embodiments provide a method, apparatus, and system for scanning an elongate structure, such as a pipe. In one illustrative example, a method is present for scanning an elongate structure. The elongate structure is scanned axially using an x-ray beam emitted by the scanner as the scanner moves along the length of the elongate structure to form an axial scan. The x-ray beam has a first orientation during the axial scanning. A location on the elongate structure having an inconsistency is detected while scanning the elongate structure axially. The elongate structure is scanned at the location with the x-ray beam in a second orientation. First data from the axial scan at the location is combined with second data from the second scan at the location to form an image of the inconsistency at the location.

Figure 1:
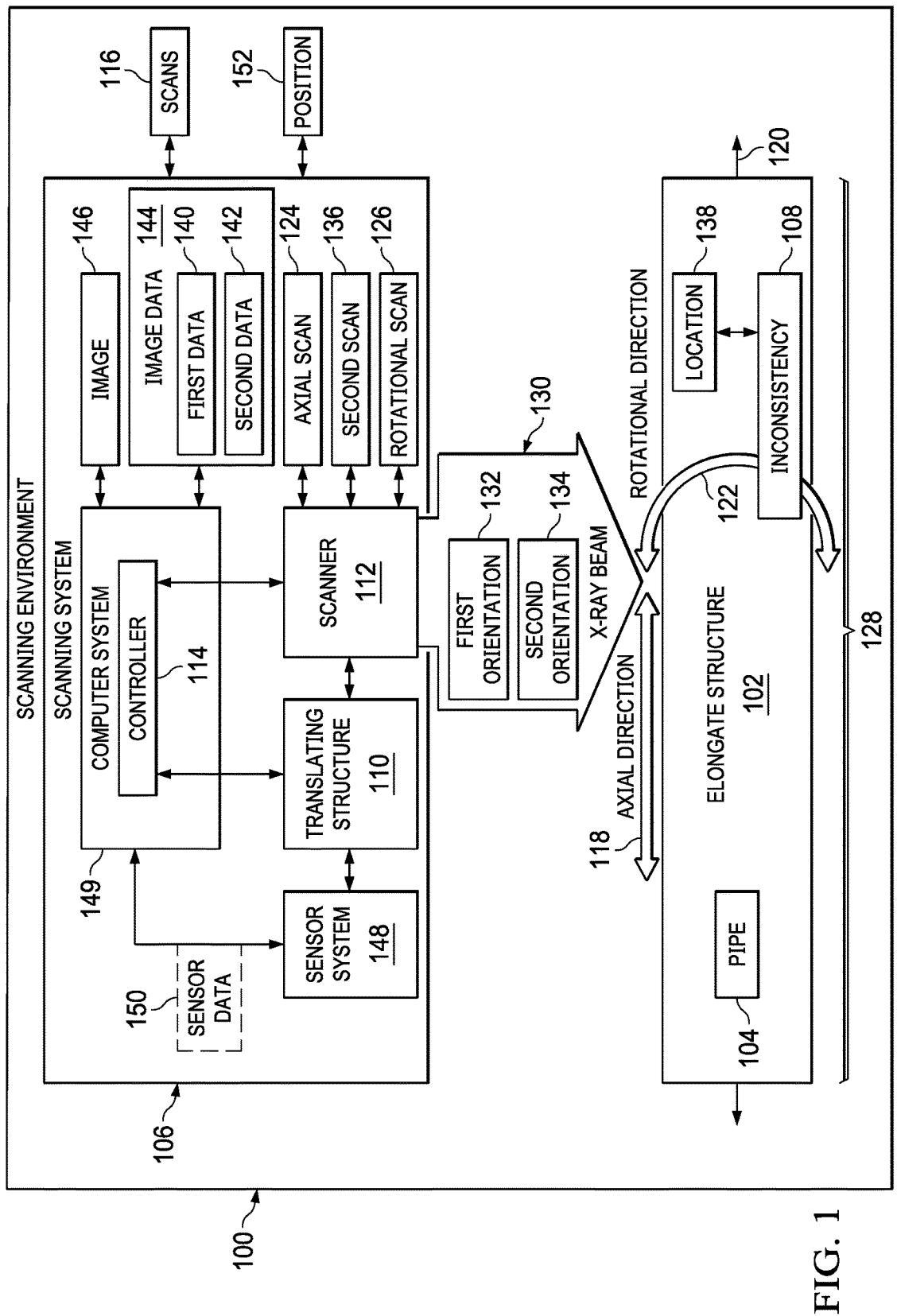
FIG. 1 is an illustration of a block diagram of a scanning environment in accordance with an illustrative embodiment.

With reference now to the figures and, specifically, with reference to FIG. 1, an illustration of a block diagram of a scanning environment is depicted in accordance with an illustrative embodiment. As depicted, scanning environment 100 includes elongate structure 102. In this illustrative example, elongate structure 102 takes the form of pipe 104. Pipe 104 carries various types of materials. For example, pipe 104 may carry at least a liquid, a gas, crude petroleum, refined petroleum, hydrogen, a fuel, oil, water, wine, beer, a natural gas, a biofuel, or other types of materials.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item B. This example also may include item A, item B, and item C, or item B and item C. Of course, any combinations of these items may be present. In some illustrative examples, "at least one of" may be, for example, without limitation, two of item A; one of item B; and ten of item C; four of item B and seven of item C; or other suitable combinations.

In this illustrative example, pipe 104 may be inspected using scanning system 106. Scanning system 106 is used to determine whether inconsistency 108 is present within pipe 104.

As depicted, inconsistency 108 is indicated by an unexpected result from elongate structure 102. For example, the unexpected result may be a value that is greater or less than a threshold. The unexpected result may be a value that is outside of a desired range.

Inconsistency 108 may take a number of different forms. For example, inconsistency 108 may be selected from a group comprising corrosion, thinning walls, an out-of-tolerance welding, an out-of-tolerance deposit, scale, a crack, and other undesired results.

In this illustrative example, scanning system 106 includes a number of different components. As depicted, scanning system 106 includes translating structure 110, scanner 112, and controller 114. Scanning system 106 is configured to perform scans 116 automatically. In other words, the need for a human operator to move scanning system 106 on elongate structure 102 is unnecessary.

As depicted, translating structure 110 is a physical hardware structure. Translating structure 110 is configured to move axially and rotationally along elongate structure 102. Translating structure 110 moves in axial direction 118 by moving in a direction coinciding with axis 120 extending centrally through pipe 104. Pipe 104 may have many axes through curves and bends in pipe 104.

Translating structure 110 can also move in rotational direction 122 by rotating on pipe 104 around axis 120. As depicted, translating structure 110 may be selected from a group comprising a motorized arm, a crawler arm, a track-based arm, and some other suitable type of structure that moves axially and rotationally.

In the illustrative example, scanner 112 is connected to translating structure 110. As used herein, a first component, scanner 112, "connected to" a second component, translating structure 110, means that the first component can be connected directly or indirectly to the second component. In other words, additional components may be present between the first component and the second component. The first component is considered to be indirectly connected to the second component when one or more additional components are present between the two components. When the first component is directly connected to the second component, no additional components are present between the two components.

As depicted, scanner 112 can perform scans 116 using a number of different types of scanning techniques. For example, scanner 112 may be selected from at least one of an x-ray scanning system, a backscatter x-ray system, or a through transmission x-ray system.

In this example, controller 114 is in communication with translating structure 110 and scanner 112. As depicted, controller 114 controls translating structure 110 to move axially along elongate structure 102 while scanner 112 performs axial scan 124 of elongate structure 102 and controls translating structure 110 to move rotationally around elongate structure 102 while scanner 112 performs rotational scan 126 of elongate structure 102.

Controller 114 enables automated scanning of elongate structure 102 in axial direction 118 for axial scan 124 and rotational direction 122 for rotational scan 126. In this manner, automated inspection of elongate structure 102 is performed without using a human operator.

During operation of scanning system 106, controller 114 moves translating structure 110 axially along length 128 of elongate structure 102 and monitors for inconsistency 108 during axial scan 124 of elongate structure 102.

In one illustrative example, scanner 112 is configured to scan elongate structure 102 utilizing x-ray beam 130 configured to move between first orientation 132 and second orientation 134 which is substantially perpendicular to first orientation 132. As depicted, controller 114 controls translating structure 110 to move axially along elongate structure 102 while scanner 112 performs axial scan 124 of elongate structure 102 using x-ray beam 130 at first orientation 132. In this illustrative example, scanner 112 generates first data 140 from axial scan 124.

As depicted, scanner 112 is configured to perform second scan 136 of elongate structure 102 using x-ray beam 130 at second orientation 134. In this example, second scan 136 is performed when inconsistency 108 is detected in axial scan 124 at location 138 on elongate structure 102. Location 138 can be described in one dimension, two dimensions, or three dimensions. For example, one dimension may be used to identify location 138 along pipe 104 using an encoder.

Scanner 112 generates second data 142 from second scan 136. First data 140 and second data 142 may be image data 144. In generating second data 142, translating structure 110 is configured to move rotationally around elongate structure 102 when scanner 112 performs second scan 136 as rotational scan 126 using x-ray beam 130 in second orientation 134.

In the illustrative example, second scan 136 may be initiated in a number of different ways. For example, translating structure 110 moves axially to return to location 138 after completing axial scan 124 of elongate structure 102 with x-ray beam 130 in first orientation 132, and moves rotationally at location 138 to perform second scan 136 as rotational scan 126 at location 138 using x-ray beam 130 in second orientation 134. In another illustrative example, translating structure 110 halts moving axially along length 128 of elongate structure 102 at location 138, and moves rotationally around location 138 to perform second scan 136 as rotational scan 126 using x-ray beam 130 in second orientation 134.

In the illustrative example, rotational scan 126 may involve moving scanner 112 in a partial or full rotation around elongate structure 102. For example, rotational scan 126 may be performed by moving scanner 112 in a number of degrees such as, two degrees, seven degrees, 25 degrees, 31 degrees, 45 degrees, 90 degrees, 111 degrees, 180 degrees, 360 degrees, or some other suitable number of degrees.

As depicted, controller 114 combines first data 140 from axial scan 124 at location 138 with second data 142 from second scan 136 in the form of rotational scan 126 at location 138 to form image 146 of inconsistency 108 at location 138.

Controller 114 may be implemented in software, hardware, firmware, or a combination thereof. When software is used, the operations performed by controller 114 may be implemented in program code configured to run on hardware, such as a processor unit. When firmware is used, the operations performed by controller 114 may be implemented in program code and data and stored in persistent memory to run on a processor unit. When hardware is employed, the hardware may include circuits that operate to perform the operations in controller 114.

In the illustrative examples, the hardware may take a form selected from at least one of a circuit system, an integrated circuit, an application specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Programmable logic devices include, for example, a programmable logic array, a programmable array logic, a field programmable logic array, a field programmable gate array, and other suitable hardware devices. Additionally, the processes may be implemented in organic components integrated with inorganic components and may be comprised entirely of organic components excluding a human being. For example, the processes may be implemented as circuits in organic semiconductors.

In the illustrative example, controller 114 may be implemented as a component in computer system 149. Computer system 149 may be located on translating structure 110, scanner 112, some combination thereof, or in a remote location from the components but in communication with the components. In yet another illustrative example, a portion of computer system 149 may be located on translating structure 110, scanner 112, or a combination thereof while another portion is in a remote location to the components.

Computer system 149 is a physical hardware system and includes one or more data processing systems. When more than one data processing system is present, those data processing systems are in communication with each other using a communications medium. The communications medium may be a network. The data processing systems may be selected from at least one of a computer, a server computer, a tablet, or some other suitable data processing system.

As depicted, scanning system 106 also includes sensor system 148. Sensor system 148 is in communication with controller 114. Sensor system 148 may be connected to translating structure 110 or may be in a number of locations.

Sensor system 148 may be comprised of at least one of an encoder, a laser range finder, a camera, an inertial measurement unit (IMU), an accelerometer, a global positioning system (GPS) unit, a gyroscope, or some other suitable type of sensor. In this illustrative example, sensor system 148 generates sensor data 150 that is used to determine position 152 of scanning system 106. Position 152 comprises a three-dimensional location of translating structure 110, scanner 112, or some combination thereof. The three-dimensional location can be described using Cartesian coordinates, polar coordinates, or some other coordinate system.

In another illustrative example, position 152 may define an axial position along length 128 of elongate structure 102. This axial position may be identified using an encoder or a laser distance meter.

Position 152 also may include an orientation of one or both of the components. The orientation may be described in a number of different ways. For example, the orientation may be described using yaw, pitch, roll, a vector, or some other suitable system. In another example, a rotational position around elongate structure 102 may be identified using an encoder.

In one illustrative example, one or more technical solutions are present that overcome a technical problem with scanning an insulated pipe for inconsistencies with a desired level of efficiency that reduces cost and time. As a result, one or more technical solutions provide a technical effect of more efficiently scanning an elongate structure, such as a pipe, using a scanning system that moves and scans axially and rotationally. One or more technical solutions provide a technical effect in which automated scanning is performed on elongate structures, such as pipes.

Further, one or more technical solutions include selecting dimensions for x-ray beam 130 that result in a technical effect of providing increased speed in scanning elongate structure 102 in an axial direction. One or more technical solutions also include selecting dimensions for x-ray beam 130 that result in a technical effect of providing increased resolution for other types of information needed to characterize inconsistency 108. Further, first data 140 from axial scan 124 and second data 142 from second scan 136 may be combined to generate image 146 of inconsistency 108 in a manner that provides an ability to analyze inconsistency 108 with a desired level of accuracy.

Automated analysis of information gathered in axial scan 124 may be used to control scanning system 106 to perform rotational scan 126 at selected locations where inconsistencies are detected. This type of automated analysis may reduce the time and expense involved in inspecting elongate structures, such as pipes.

Further, in the illustrative example, one or more technical solutions provide a technical effect in which placing or attaching external guides or support is unnecessary. As a result, the cost and time for inspecting elongate structure 102 may be reduced as compared to currently available techniques. In the illustrative examples, scanning system 106 operates as a high-speed pipe inspection system when elongate structure 102 takes the form of pipe 104.

As a result, computer system 149 operates as a special purpose computer system in which controller 114 in computer system 149 enables controlling operation of a scanning system, such as a mobile scanning arm performing axial and rotational scans. In particular, controller 114 transforms computer system 149 into a special purpose computer system as compared to currently available general computer systems that do not have controller 114.

Figure 2:
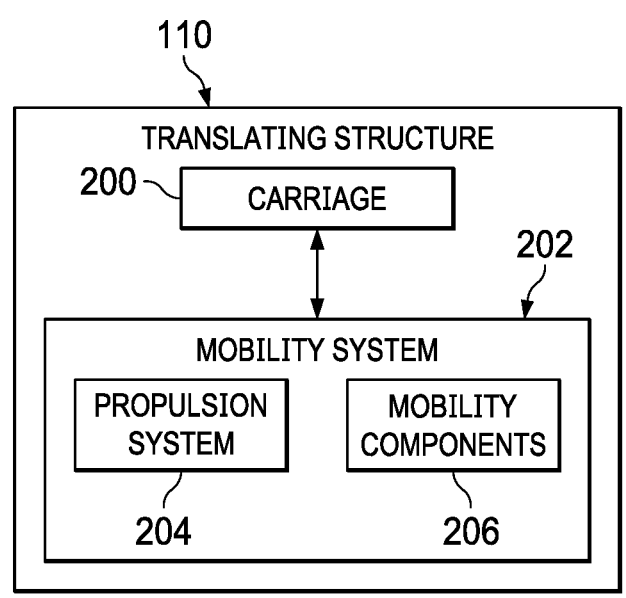
FIG. 2 is an illustration of a block diagram of a translating structure in accordance with an illustrative embodiment.

Turning next to FIG. 2, an illustration of a block diagram of a translating structure is depicted in accordance with an illustrative embodiment. In the illustrative examples, the same reference numeral may be used in more than one figure. This reuse of a reference numeral in different figures represents the same element in the different figures.

In this depicted example, translating structure 110 includes a number of different components. As depicted, translating structure 110 comprises carriage 200 and mobility system 202.

In this example, carriage 200 is a physical structure that is configured to attach itself to elongate structure 102 shown in block form in FIG. 1. For example, carriage 200 holds scanning system 106, shown in block form in FIG. 1, on elongate structure 102 such that mobility system 202 is able to move carriage 200 axially and rotationally with respect to elongate structure 102.

As depicted, mobility system 202 comprises propulsion system 204 and mobility components 206. The components are selected to move carriage 200 axially and rotationally. Propulsion system 204 may be an electrically controlled propulsion system. Propulsion system 204 may be, for example, without limitation, selected from at least one of an internal combustion engine, an electric engine, or some other suitable propulsion system.

Mobility components 206 provide carriage 200 with the capability to move in a number of directions. Mobility components 206 may be comprised of at least one of a roller, a wheel, a holonomic wheel, a track, or other suitable components. As used herein, a holonomic wheel (or an omni wheel) is one that is capable of moving in multiple directions across a surface.

Figure 3:
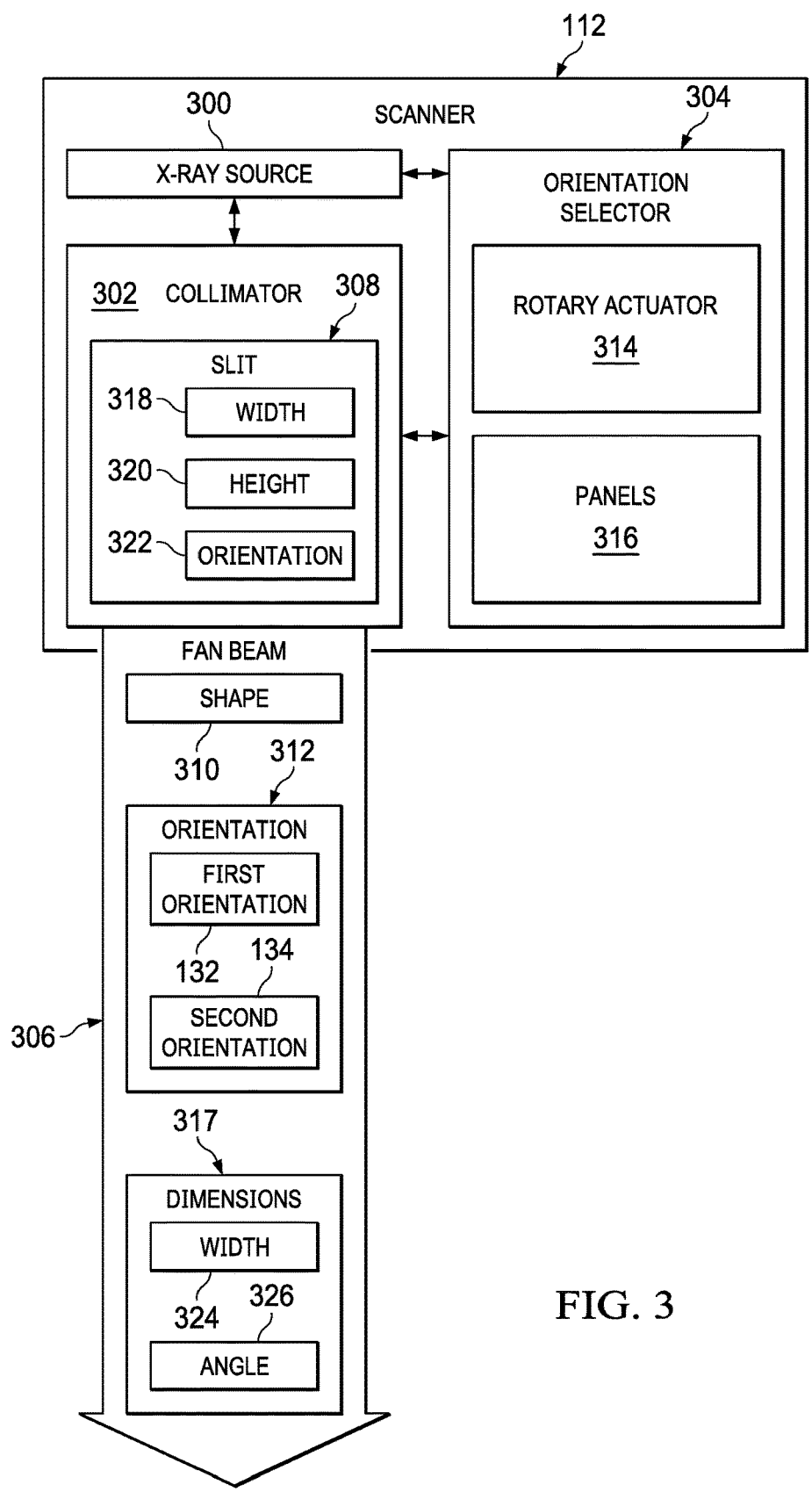
FIG. 3 is an illustration of a block diagram of a scanner in accordance with an illustrative embodiment.

With reference now to FIG. 3, an illustration of a block diagram of a scanner is depicted in accordance with an illustrative embodiment. As depicted, the components in this figure illustrate one example of an implementation for scanner 112. In this illustrative example, scanner 112 comprises x-ray source 300, collimator 302, and orientation selector 304.

X-ray source 300 is a source of x-rays that are emitted from scanner 112 as fan beam 306 in this illustrative example. Fan beam 306 is an example of an implementation for x-ray beam 130 shown in block form in FIG. 1. X-ray source 300 may be an x-ray tube.

In the illustrative example, collimator 302 is a device that narrows a beam of particles or waves to form fan beam 306. For example, slit 308 is present in collimator 302 that defines shape 310 of fan beam 306. Slit 308 has a rectangular shape, in this example, that causes shape 310 of fan beam 306 to be rectangular. Further, fan beam 306 has orientation 312.

Orientation selector 304 is a device configured to change orientation 312 of fan beam 306. As depicted, orientation selector 304 can change orientation 312 of x-ray beam 130 between first orientation 132 and second orientation 134.

For example, orientation selector 304 may take the form of rotary actuator 314. X-ray source 300 and collimator 302 can be connected to rotary actuator 314. Rotary actuator 314 can rotate the components such that orientation 312 of fan beam 306 changes between first orientation 132 and second orientation 134. In this manner, the x-ray beam, fan beam 306, changes between first orientation 132 and second orientation 134 by rotating collimator 302 in scanner 112.

In another example, orientation selector 304 may be implemented as part of collimator 302. In this example, panels 316 in collimator 302 are configured to form slit 308. Panels 316 can be used to define dimensions 317 for fan beam 306. In this illustrative example, dimensions 317 comprise width 318 for slit 308 and height 320 for slit 308.

Panels 316 can be adjusted to change width 318 and height 320 of slit 308 in a manner that changes orientation 322 of slit 308. The dimensions of slit 308 determine the dimensions of fan beam 306. For example, width 318 of slit 308 determines width 324 of fan beam 306. Height 320 of slit 308 determines angle 326 for fan beam 306. As a result, x-ray beam 130, in the form of fan beam 306, changes between first orientation 132 and second orientation 134 by changing dimensions 317 of slit 308 in collimator 302 of scanner 112. In the illustrative example, the change between first orientation 132 and second orientation 134 is such that the two orientations are substantially perpendicular to each other. In other words, slit 308 in collimator 302 may be rotated about 90 degrees. The change may be made to have a narrow fan beam along an elongate piece, such as a pipe, relative to the scan direction. In this example, the selection of the orientation is to have perpendicularity of a narrow fan beam along an elongated piece, relative to the scan direction.

The illustration of scanning environment 100 in FIG. 1 and the different components in this environment in FIGS. 1-3 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of the blocks may be combined, divided, or combined and divided into different blocks when implemented in an illustrative embodiment.

For example, elongate structure 102 may take other forms other than pipe 104. In other illustrative examples, elongate structure 102 may be selected from one of a drum, a conduit, a structural cable, a stringer, a structural beam, a wind turbine blade, a station, a piling, and other suitable types of elongate structures.

Figure 4:
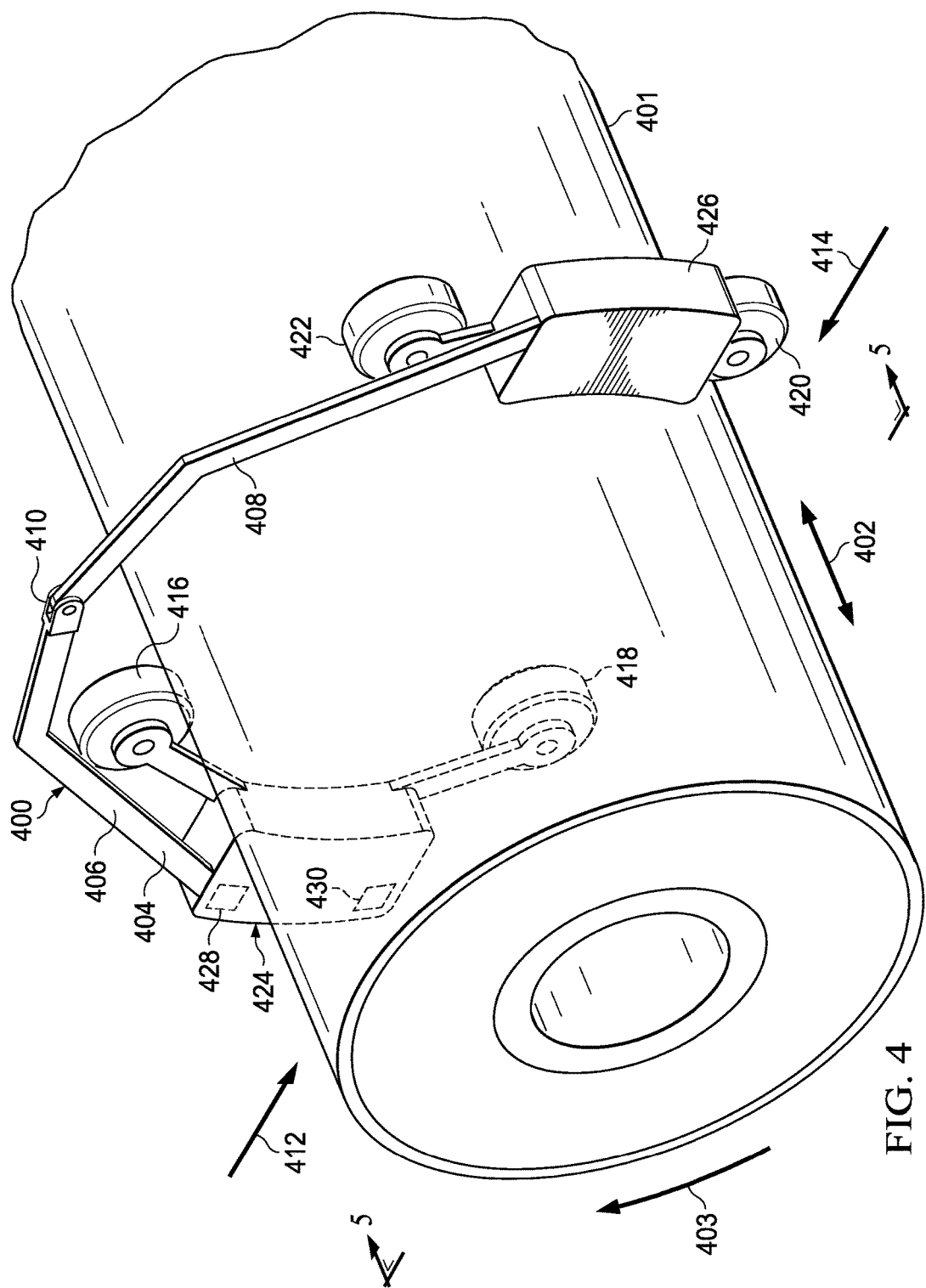
FIG. 4 is an illustration of a scanning system attached to an insulated pipe in accordance with an illustrative embodiment.

With reference now to FIG. 4, an illustration of a scanning system attached to an insulated pipe is depicted in accordance with an illustrative embodiment. As depicted, mobile scanning arm 400 is clamped on insulated pipe 401. Mobile scanning arm 400 can move axially as shown by arrow 402 and rotationally as shown by arrow 403 to scan insulated pipe 401.

Mobile scanning arm 400 has a number of different components. In this illustrative example, mobile scanning arm 400 includes carriage 404, which is an example of one physical implementation for carriage 200 shown in block form in FIG. 2 for translating structure 110 shown in FIG. 1.

In this illustrative example, carriage 404 includes structural member 406, structural member 408, and biased joint 410. Biased joint 410 connects structural member 406 and structural member 408 to each other. Biased joint 410 causes structural member 406 to be biased in the direction of arrow 412 and structural member 408 to be biased in the direction of arrow 414. This biasing is designed to allow carriage 404 to clamp itself to insulated pipe 401 or some other elongate structure for scanning operations.

Biased joint 410 may be implemented using a number of different mechanisms. For example, biased joint 410 may be a spring-loaded joint, a hydraulic piston, a screw actuator, a slide and snap adjustment system, or some other suitable mechanism.

Mobile scanning arm 400 includes holonomic wheel unit 416 (e.g. a unit including a holonomic wheel), holonomic wheel unit 418, holonomic wheel unit 420, and holonomic wheel unit 422. The wheel units are examples of components in mobility system 202 shown in block form in FIG. 2.

As depicted, holonomic wheel unit 416 and holonomic wheel unit 418 are connected to housing 424. Holonomic wheel unit 420 and holonomic wheel unit 422 are connected to housing 426. The wheel units include motors, as well as wheels, and represent an implementation for propulsion system 204 and mobility components 206 shown in block form in FIG. 2. Holonomic wheel unit 416, holonomic wheel unit 418, holonomic wheel unit 420, and holonomic wheel unit 422 allow for independent rotational movement and axial movement from the same set of wheel units.

As depicted, scanner 428 is located within housing 424 of mobile scanning arm 400. In this illustrative example, scanner 428 takes the form of a backscatter x-ray system.

In this example, controller 430 is an example of one implementation for controller 114 shown in block form in FIG. 1. As depicted, controller 430 is located within housing 424 and controls the operation of mobile scanning arm 400. Controller 430 controls the movement of mobile scanning arm 400 and the operation of scanner 428 in performing scans.

Controller 430 is in communication with scanner 428. Controller 430 is configured to receive data from scanner 428 and control the operation of mobile scanning arm 400 using the data. Controller 430 is configured to generate images using data received from scanner 428. The images can be used to visualize the characteristics about inconsistencies that may be found in insulated pipe 401. The characteristics may include size, type of inconsistency, location of inconsistency, and other information. The type of inconsistency may include the amount or degree of corrosion, cracks, voids, missing insulation, or other types of undesired features or conditions.

As depicted, mobile scanning arm 400 performs an axial scan moving in the direction of arrow 402 along the length of insulated pipe 401. The scan can be performed by scanner 428 emitting a fan beam in a first orientation along insulated pipe 401 looking for changes in the detected backscatter.

For example, the signal from the backscatter may be at a substantially consistent level. A drop in the backscatter signal may indicate that an inconsistency is present. If a drop in the level of backscatter signals is detected, mobile scanning arm 400 can move back to the location where the drop was identified. Mobile scanning arm 400 can then perform a scan with scanner 428 emitting a fan beam in a second orientation. With the data from the axial scan and the second scan at the location, an image can be generated using this data to provide more information about the inconsistency.

The illustration mobile scanning arm 400 in FIG. 4 is meant as an example of one implementation for translating structure 110 in scanning system 106 in FIG. 1. In another illustrative example, translating structure 110 may take a form such as a robotic arm located on a stationary or mobile platform. When a mobile platform is present, the mobile platform can traverse a surface that is parallel to the elongate structure. In another illustrative example, translating structure 110 may be an airborne platform, such as a drone, configured to carry scanner 112.

Figure 5:
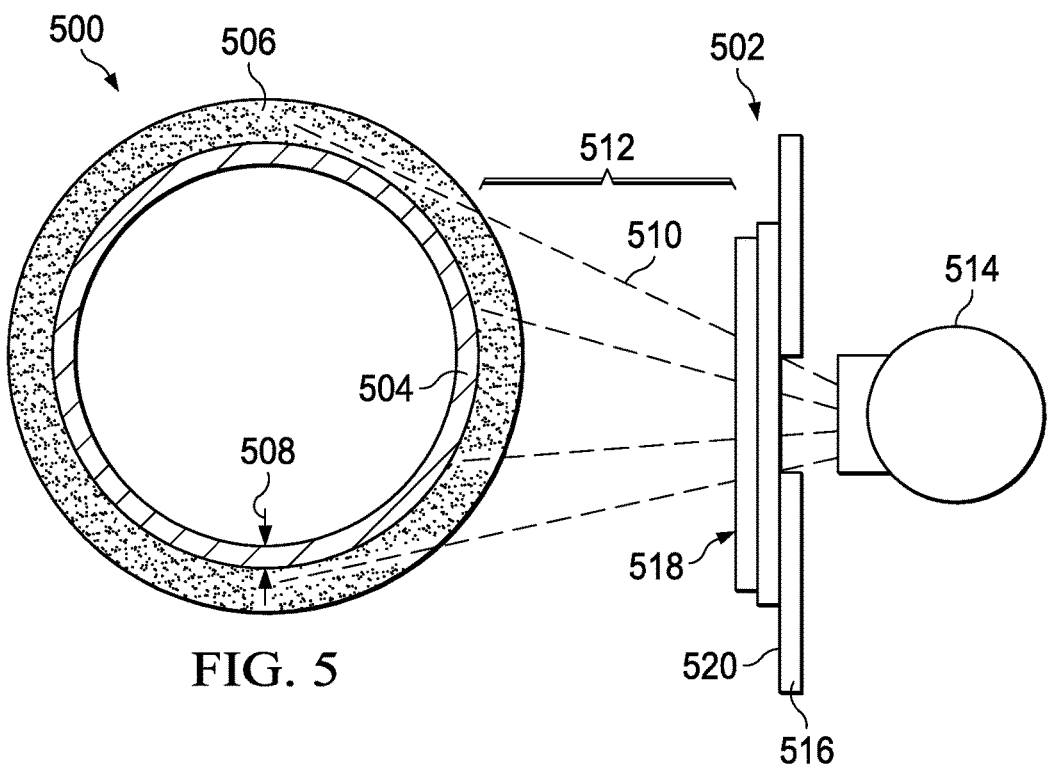
FIG. 5 is an illustration of a cross-sectional view of an insulated pipe with a scanner in accordance with an illustrative embodiment.

With reference next to FIG. 5, an illustration of a cross-sectional view of an insulated pipe with a scanner is depicted in accordance with an illustrative embodiment. As depicted, a cross-section of insulated pipe 500 with scanner 502 positioned relative to insulated pipe 500 is shown taken along separated lines 5-5 in FIG. 4. Scanner 502 is an example of one implementation for scanner 112 shown in block form in FIG. 1. Scanner 502 also may be an example of one implementation in which scanner 428 may be implemented in FIG. 5.

As depicted, in this example, insulated pipe 500 includes pipe 504 and insulation 506. Inconsistencies in pipe 504 can be detected by identifying wall thickness 508 of insulated pipe 500. Wall thickness 508 is identified using fan beam 510 emitted from scanner 502 in first orientation 512 at a first distance from insulated pipe 500 to form an axial scan of insulated pipe 500 along the length of insulated pipe 500.

As depicted, scanner 502 includes x-ray source 514, collimator 516, and detector system 518. In this illustrative example, front side 520 of scanner 502 faces insulated pipe 500. As depicted, detector system 518 is implemented using solid-state detectors. The solid-state detectors may be, for example, semiconductor detectors that convert x-ray photons to an electrical charge in a manner that allows for generating a digital image.

Detector system 518 detects backscatter from pipe 504 in response to fan beam 510. The detection of the backscatter can be used to identify wall thickness 508 of pipe 504.

Figure 6:
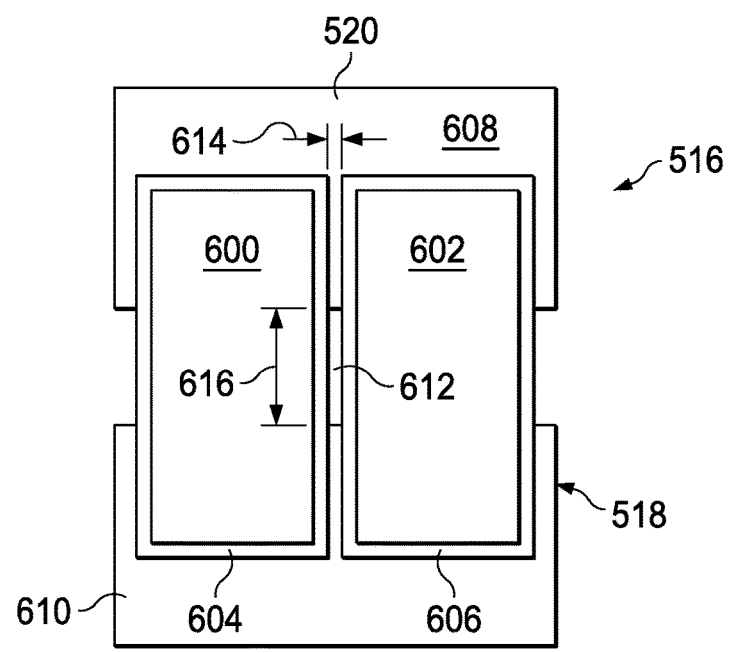
FIG. 6 is an illustration of a front side of a scanner in accordance with an illustrative embodiment.

With reference next to FIG. 6, an illustration of a front side of a scanner is depicted in accordance with an illustrative embodiment. In this illustrative example, a view of front side 520 of scanner 502 of FIG. 5 is shown.

In this view, detector system 518 is comprised of detector 600 and detector 602. Detector 600 is connected to panel 604, and detector 602 is connected to panel 606 in collimator 516. These panels, along with panel 608 and panel 610, can be adjusted to define dimensions for slit 612.

As depicted, panel 604 and panel 606 define width 614 for slit 612. Width 614 of slit 612 defines the width of a fan beam. Panel 608 and panel 610 define height 616 of slit 612. Height 616 is adjusted to set an angle for the fan beam.

Figure 7:
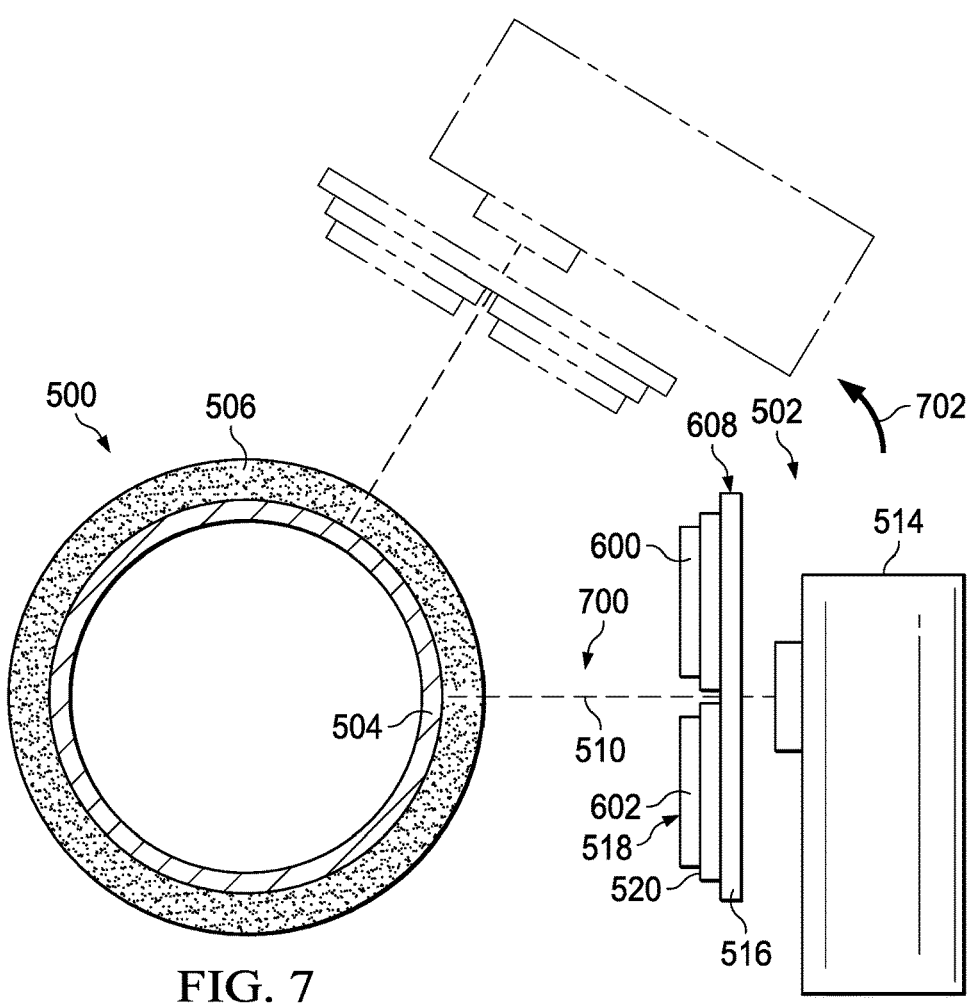
FIG. 7 is an illustration of a cross-sectional view of an insulated pipe with a scanner in accordance with an illustrative embodiment.

With reference next to FIG. 7, an illustration of a cross-sectional view of an insulated pipe with a scanner is depicted in accordance with an illustrative embodiment. In this figure, scanner 502 has been rotated clockwise relative to front side 520. The rotation of scanner 502 may be performed using a rotary actuator or some other suitable mechanism. This rotation of scanner 502 causes slit 612 of FIG. 6 to rotate such that fan beam 510 moves from first orientation 512 as shown in FIG. 5 to second orientation 700 as shown in FIG. 7. In this illustrative example, a rotation of about 90 degrees is made between first orientation 512 and second orientation 700. Although the example illustrates using two orientations that are 90 degrees, other angles may be used. For example, more than two different angles may be used and those images may be combined. For example, three scans may be made at 120 degrees from each other and the data from those scans can be combined to form the image.

Scanner 502 is moved rotationally around insulated pipe 500 in the direction of arrow 702 to another position with scanner 502 shown in phantom at the new position. Scanner 502 performs a second scan while being rotated in the direction of arrow 702 in this example. In this manner, data for a scan of the circumference of insulated pipe 500 may be generated in the location where an out-of-tolerance signal was detected.

Figure 8:
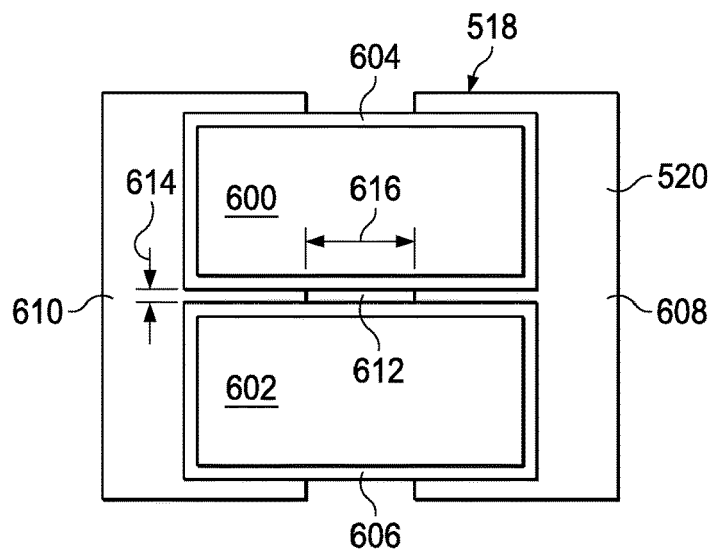
FIG. 8 is an illustration of a front side of a scanner in accordance with an illustrative embodiment.

With reference now to FIG. 8, an illustration of a front side of a scanner is depicted in accordance with an illustrative embodiment. A view of front side 520 of scanner 502 is shown in this figure. As depicted, slit 612 has been rotated 90 degrees to move from first orientation 512 of FIG. 5 to second orientation 700 of FIG. 7.

The illustration of scanner 502 and the different components in scanner 502 in FIGS. 5-8 have been provided for purposes of illustrating an example of one implementation of scanner 112 shown in block form in FIG. 1. The illustrations of the components are not meant to limit the manner in which other illustrative examples may be implemented.

For example, collimator 516 has been shown as being rotated to change the orientation of fan beam 510 from first orientation 512 to second orientation 700. This rotation has been described as being performed using a rotary actuator. In other illustrative examples, the orientation of fan beam 510 may be adjusted by changing the dimensions of slit 612. The dimensions can be changed by adjusting panel 604, panel 606, panel 608, and panel 610. The adjustment may be made such that width 614 increases to become height 616 and height 616 decreases to become width 614. In this manner, slit 612 can be rotated without rotating collimator 516. The adjustments of the panels can be made using actuators or other suitable mechanisms.

With reference next to FIG. 9, an illustration of an axial scan is depicted in accordance with an illustrative embodiment. In this illustrative example, axial scan 900 is performed by moving a scanner in the direction of arrow 902. Fan beam 904 is shown in first orientation 906. In this example, width 908 and height 910 are selected for speed in scanning an elongate structure, such as a pipe, in an axial direction. In the illustrative example, width 908 is the narrower dimension between width 908 and height 910. Width 908 is often, but not always, in the direction in which scanning is performed, which is in axial direction in this figure.

In selecting dimensions for fan beam 904, a narrowing width 908 of fan beam 904 increases the spatial resolution of inconsistencies. This narrowing, however, reduces the number of x-rays that pass through the elongate structure. When width 908 is narrowed, the speed at which fan beam 904 moves is reduced to obtain sufficient signal-to-noise ratio to detect inconsistencies. As width 908 is increased, the wider fan beam allows faster scanning in the axial direction. Width 908 may be narrowed and re-scanning axially may occur once an inconsistency is detected, to obtain a better characterization. Width 908 also may be reduced, to obtain increased resolution in the rotational direction before combining the data to generate an image.

Data 912 in axial scan 900 is generated from moving fan beam 904 in the direction of arrow 902. Data 912 may not be suitable for generated images with a desired resolution without additional data. Data 912, however, can provide an indication of a location where an inconsistency may be present.

As depicted, out-of-tolerance location 914 is present in data 912. Out-of-tolerance location 914 is a location at which an inconsistency is present. For example, out-of-tolerance location 914 is a location in which a thinning of the pipe wall may have occurred.

With reference next to FIG. 10, an illustration of a second scan is depicted in accordance with an illustrative embodiment. In this illustrative example, second scan 1000 is a rotational scan around the circumference of a pipe in the direction of arrow 1002. Second scan 1000 is performed at out-of-tolerance location 914 identified in data 912 generated from axial scan 900 in FIG. 9.

In this illustrative example, fan beam 904 has width 1004 and height 1006. The selection of width 1004 and height 1006 is made to increase at least one of resolution or other information that can be generated at out-of-tolerance location 914 in contrast to the selection of width 908 and height 910 in FIG. 9 for speed. In this example, fan beam 904 has second orientation 1007. Second scan 1000 is a rotational scan in this example.

Width 1004 of fan beam 904 may be selected to cover an area of interest. Increasing width 1004 to cover more than the area of interest may reduce efficiency and waste x-ray flux. Further, reducing the distance of the transmitted x-rays increases the quality of detection. Also, reducing the distance reduces the parallax caused by a non-zero x-ray source spot size, which produces a 'fuzzy' slit for fan beam 904. Also, reducing width 1004 increases resolution.

As depicted, data 1008 is generated in second scan 1000 from moving fan beam 904 in the direction of arrow 1002. Data 1008 from second scan 1000 indicates the presence of an inconsistency at location 1010.

Turning to FIG. 11, an illustration of an image generated from an axial scan and a second scan of a pipe is depicted in accordance with an illustrative embodiment. In this example, data 1100 is generated from combining data 912 in FIG. 9 and data 1008 in FIG. 10. The combining may involve projecting the portion of data 1008 from out-of-tolerance location 914 onto data 912 of FIG. 9 from location 1010 of FIG. 10.

The combining of data 912 and data 1008 results in data 1100 in the form of image 1102. A mapping of features regarding the inconsistency may be seen in image 1102. These features may include at least one of flaw size, shape, severity, or other characteristics of the inconsistency.

Figure 12:
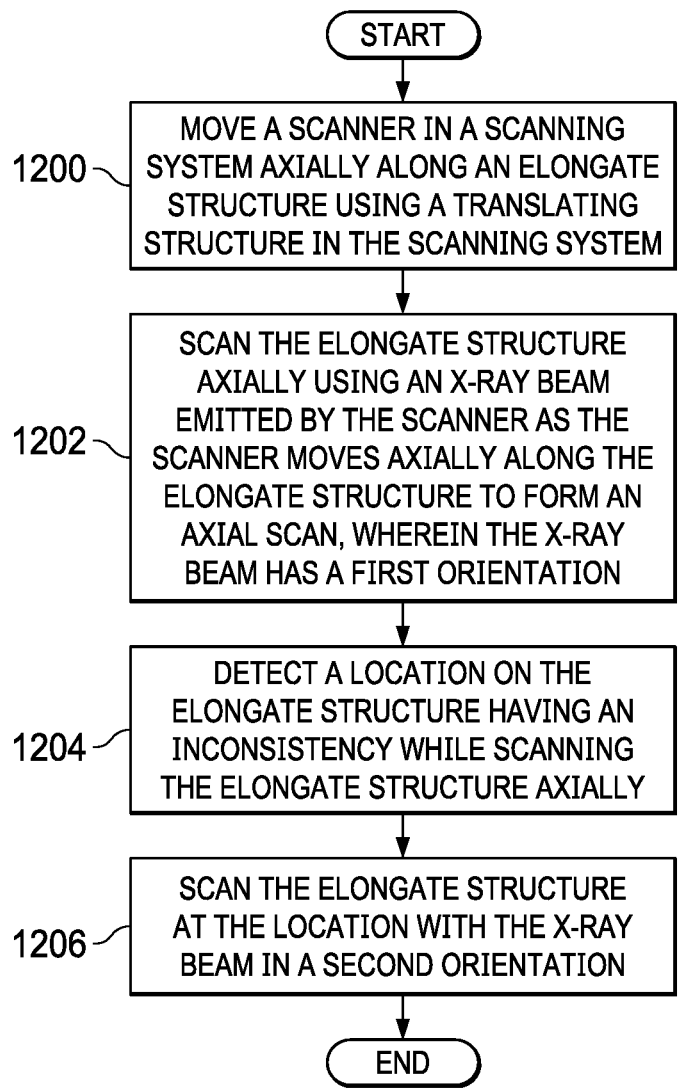
FIG. 12 is an illustration of a flowchart of a process for scanning an elongate structure in accordance with an illustrative embodiment.

Turning next to FIG. 12, an illustration of a flowchart of a process for scanning an elongate structure is depicted in accordance with an illustrative embodiment. The process illustrated in FIG. 12 can be implemented in scanning environment 100 as shown in block form in FIGS. 1-3 using scanning system 106. For example, one or more operations may be implemented in controller 114 shown in block form in FIG. 1 in the form of software, hardware, or some combination thereof to control the operation of scanning system 106.

The process begins by moving a scanner in a scanning system axially along an elongate structure using a translating structure in the scanning system (operation 1200). The process scans the elongate structure axially using an x-ray beam emitted by the scanner as the scanner moves axially along the elongate structure to form an axial scan, wherein the x-ray beam has a first orientation (operation 1202). In this illustrative example, the axial scan is performed for speed. The x-ray beam may take the form of a fan with dimensions that are selected for increasing the speed at which the axial scan can be performed.

The process detects a location on the elongate structure having an inconsistency while scanning the elongate structure axially (operation 1204). The process scans the elongate structure at the location with the x-ray beam in a second orientation (operation 1206). In this orientation, the dimensions of the x-ray beam also may be selected to increase at least one of resolution or other information that can be generated at the location in contrast to selecting the dimensions for speed. The process terminates thereafter.

Figure 13:
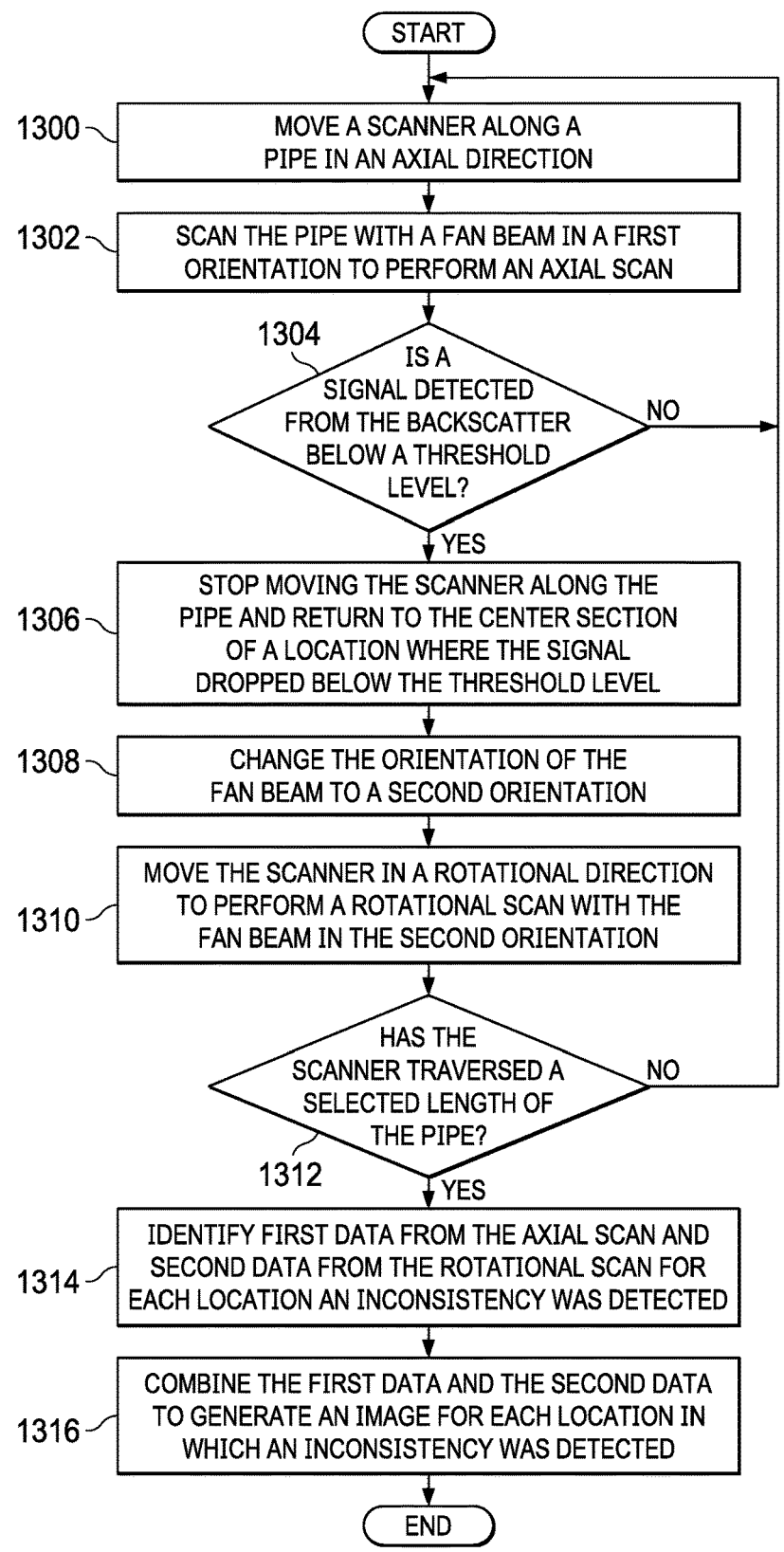
FIG. 13 is an illustration of a flowchart of a process for scanning a pipe in accordance with an illustrative embodiment.

With reference to FIG. 13, an illustration of a flowchart of a process for scanning a pipe is depicted in accordance with an illustrative embodiment. The process illustrated in FIG. 13 may be implemented using scanning system 106 to scan pipe 104 shown in block form in FIG. 1.

The process begins by moving a scanner along a pipe in an axial direction (operation 1300). The process scans the pipe with a fan beam in a first orientation to perform an axial scan (operation 1302). The dimensions of the fan beam are selected to rapidly scan a pipe.

A determination is made as to whether a signal detected from the backscatter is below a threshold level (operation 1304). The threshold level may be a minimum thickness for a pipe, in which a signal below that threshold indicates the presence of an inconsistency, such as corrosion, thinning, or spalling damage. If the signal is not below the threshold level, the process returns to operation 1300.

Otherwise, the process stops moving the scanner along the pipe and returns to the center section at a location where the signal dropped below the threshold level (operation 1306). In operation 1306, the scanner is moved back to the center section at the location where the signal was detected as dropping below the threshold level.

The process changes the orientation of the fan beam to a second orientation (operation 1308). In operation 1308, the orientation can be changed by rotating the collimator containing the slit. In another illustrative example, panels or other structures defining the slit can be adjusted or reconfigured to change the orientation of the slit. The dimensions of the slit are selected such that the fan beam has dimensions that are selected for generating information about the inconsistency. Information can be generated with an increased resolution for images.

The process moves the scanner in a rotational direction to perform a rotational scan with the fan beam in the second orientation (operation 1310).

A determination is then made as to whether the scanner has traversed a selected length of the pipe (operation 1312). The selected length may be a portion or all of the pipe depending on the implementation. If the scanner has not traversed the selected length of pipe, the process returns to operation 1300.

With reference again to operation 1312, if the scanner has traversed the selected length of the pipe, the process identifies first data from the axial scan and second data from the rotational scan for each location where an inconsistency was detected (operation 1314). The process combines the first data and the second data to generate an image for each location in which an inconsistency was detected (operation 1316). The process terminates thereafter.

Figure 14:
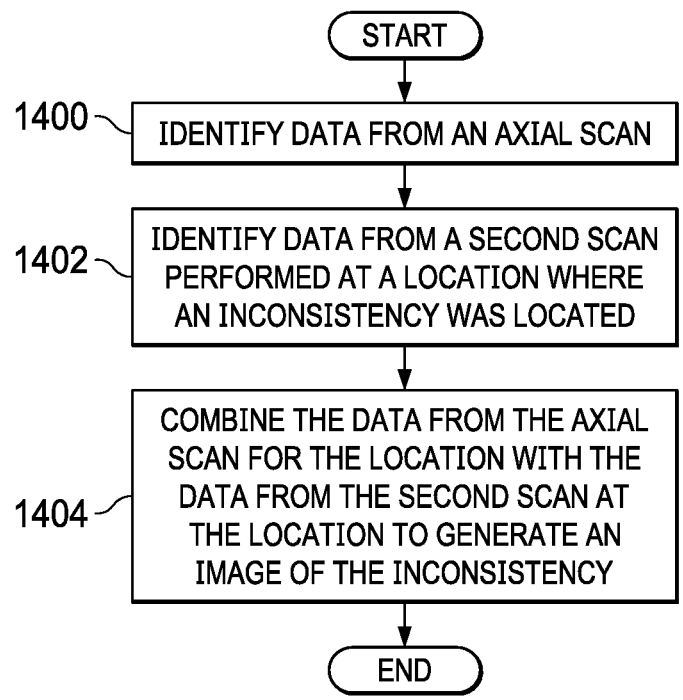
FIG. 14 is an illustration of a flowchart of a process for generating an image of an inconsistency in accordance with an illustrative embodiment.

With reference next to FIG. 14, an illustration of a flowchart of a process for generating an image of an inconsistency is depicted in accordance with an illustrative embodiment. The process illustrated in FIG. 14 can be implemented in controller 114 to generate image 146 from first data 140 and second data 142, all depicted in block form in FIG. 1.

The process begins by identifying data from an axial scan (operation 1400). The process identifies data from a second scan performed at a location where an inconsistency was located (operation 1402).

The process combines the data from the axial scan for the location with the data from the second scan at the location to generate an image of the inconsistency (operation 1404). The process terminates thereafter. Operation 1404 can be performed using currently available software that combines images as a sum. Areas of the image that are above a threshold will indicate an inconsistency. Steps may be performed, such as filtering, based on size. Further, local averaging can be performed to smooth the image. Intensities for different types of inconsistencies can also be filtered and displayed as different shapes or colors.

With images generated from the scans at different orientations, locations where inconsistencies were detected can be further accessed, reworked, or replaced. As a result, scans of the elongate structures, such as pipes, may be performed more efficiently.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. For example, one or more of the blocks may be implemented as program code, hardware, or a combination of program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams may be implemented using special purpose hardware systems that perform the different operations or combinations of special purpose hardware and program code run by the special purpose hardware.

An operation may be included to mark locations where inconsistencies were detected. The locations may be automatically marked by scanning system 106 as scanning system 106 in FIG. 1 performs scans. This marking may be performed using paint, tape, micro dot, or some other suitable marking technique.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Figure 15:
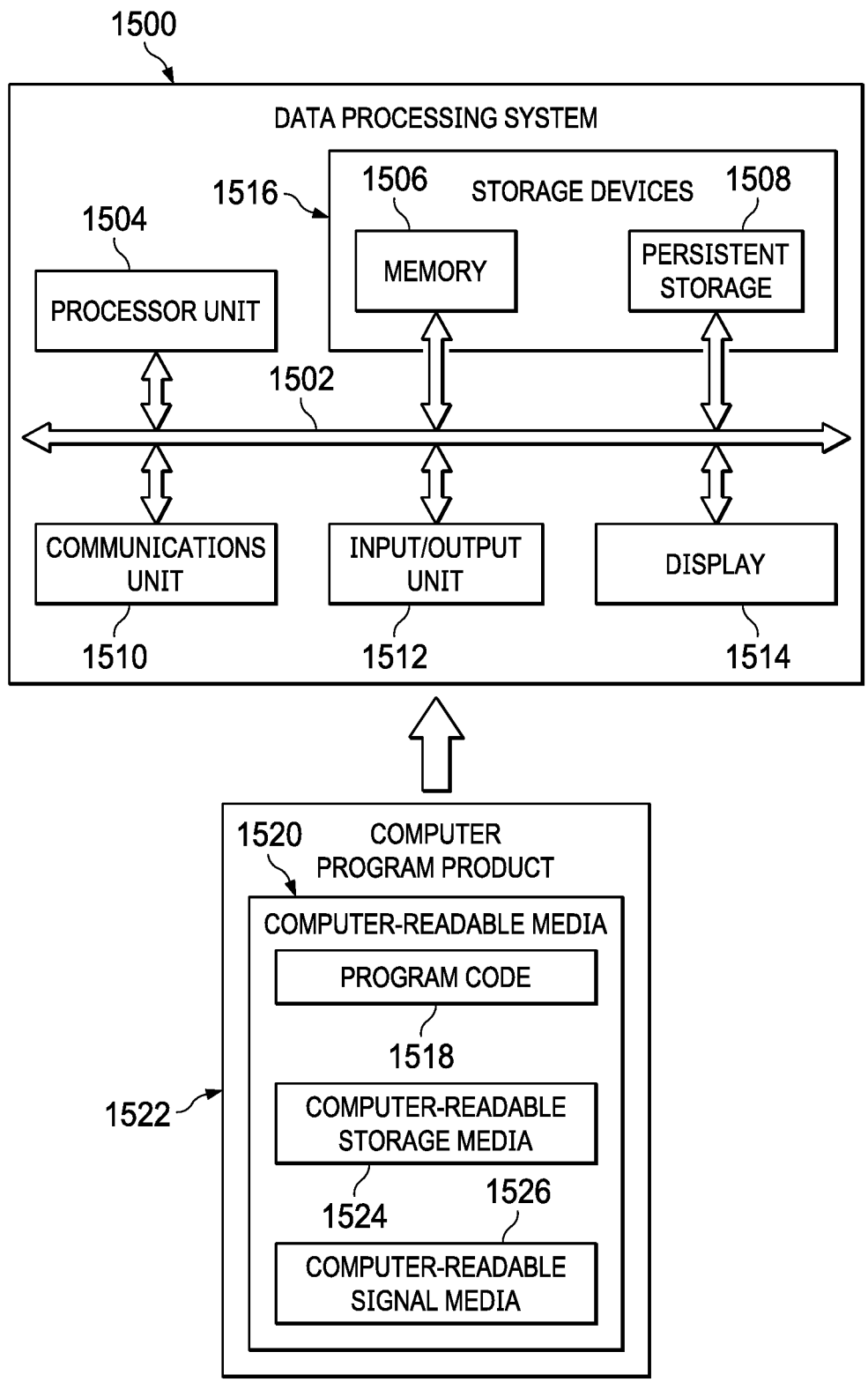
FIG. 15 is an illustration of a block diagram of a data processing system in accordance with an illustrative embodiment.

Turning now to FIG. 15, an illustration of a block diagram of a data processing system is depicted in accordance with an illustrative embodiment. Data processing system 1500 may be used to implement computer system 149 in FIG. 1. In this illustrative example, data processing system 1500 includes communications framework 1502, which provides communications between processor unit 1504, memory 1506, persistent storage 1508, communications unit 1510, input/output (I/O) unit 1512, and display 1514. In this example, communications framework 1502 may take the form of a bus system.

Processor unit 1504 serves to execute instructions for software that may be loaded into memory 1506. Processor unit 1504 may be a number of processors, a multi-processor core, or some other type of processor, depending on the particular implementation.

Memory 1506 and persistent storage 1508 are examples of storage devices 1516. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1516 may also be referred to as computer-readable storage devices in the illustrative examples. Memory 1506, may be, for example, a random-access memory or any other suitable volatile or non-volatile storage device. Persistent storage 1508 may take various forms, depending on the particular implementation.

For example, persistent storage 1508 may contain one or more components or devices. For example, persistent storage 1508 may be a hard drive, a solid state hard drive, a flash memory, a rewritable optical disk, a rewritable magnetic tape, or some combination of the above. The media used by persistent storage 1508 also may be removable. For example, a removable hard drive may be used for persistent storage 1508.

Communications unit 1510, in the illustrative examples, provides for communications with other data processing systems or devices. In the illustrative examples, communications unit 1510 is a network interface card.

Input/output unit 1512 allows for input and output of data with other devices that may be connected to data processing system 1500. For example, input/output unit 1512 may provide a connection for user input through at least one of a keyboard, a mouse, or some other suitable input device. Further, input/output unit 1512 may send output to a printer. Display 1514 provides a mechanism to display information to a user.

Instructions for at least one of the operating system, applications, or programs may be located in storage devices 1516, which are in communication with processor unit 1504 through communications framework 1502. The processes of the different embodiments may be performed by processor unit 1504 using computer-implemented instructions, which may be located in a memory, such as memory 1506.

These instructions are referred to as program code, computer usable program code, or computer-readable program code that may be read and executed by a processor in processor unit 1504. The program code in the different embodiments may be embodied on different physical or computer-readable storage media, such as memory 1506 or persistent storage 1508.

Program code 1518 is located in a functional form on computer-readable media 1520 that is selectively removable and may be loaded onto or transferred to data processing system 1500 for execution by processor unit 1504. Program code 1518 and computer-readable media 1520 form computer program product 1522 in the illustrative examples. In one example, computer-readable media 1520 may be computer-readable storage media 1524 or computer-readable signal media 1526.

In the illustrative examples, computer-readable storage media 1524 is a physical or tangible storage device used to store program code 1518 rather than a medium that propagates or transmits program code 1518.

Alternatively, program code 1518 may be transferred to data processing system 1500 using computer-readable signal media 1526. Computer-readable signal media 1526 may be, for example, a propagated data signal containing program code 1518. For example, computer-readable signal media 1526 may be at least one of an electromagnetic signal, an optical signal, or any other suitable type of signal. The signals may be transmitted over at least one of communications links, such as wireless communications links, optical fiber cable, coaxial cable, a wire, or any other suitable type of communications link.

The different components illustrated for data processing system 1500 are not meant to provide architectural limitations to the manner in which different embodiments may be implemented. The different illustrative embodiments may be implemented in a data processing system including components in addition to or in place of those illustrated for data processing system 1500. Other components shown in FIG. 15 can be varied from the illustrative examples shown. The different embodiments may be implemented using any hardware device or system capable of running program code 1518.

In one illustrative example, one or more technical solutions are present that overcome a technical problem with scanning an insulated pipe for inconsistencies with a desired level of efficiency that reduces cost and time.

As a result, the illustrative examples provide an ability to more efficiently scan an elongate structure, such as a pipe, using a scanning system that moves and scans axially and rotationally. Further, the illustrative example includes selecting dimensions for an x-ray beam in the form of a fan beam that are selected to increase the speed at which an elongate structure is scanned. Further, the illustrative example also includes selecting dimensions for the fan beam that increase resolution for other types of information needed to characterize an inconsistency. With the two scans in two orientations, the data from the scans can be combined to generate an image with a desired level of information to characterize and analyze an inconsistency.

Further, automated analysis of information gathered in an axial scan can be used to control the scanning system to perform a rotational scan at selected locations where inconsistencies are detected. This type of automated analysis may reduce the time and expense involved in inspecting elongate structures, such as pipes.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A scanning system comprising:
a translating structure configured to move axially along an elongate structure;
a scanner connected to the translating structure, wherein the scanner is configured to scan the elongate structure utilizing an x-ray beam configured to have a first orientation and a second orientation substantially perpendicular to the first orientation; and
a controller in communication with the translating structure and the scanner, wherein the controller controls the translating structure to move axially along the elongate structure while the scanner performs an axial scan of the elongate structure using the x-ray beam at the first orientation and performs a second scan of the elongate structure using the x-ray beam at the second orientation when an inconsistency is detected in the axial scan at a location on the elongate structure.

2. The scanning system of claim 1, wherein the controller combines first data from the axial scan at the location with second data from the second scan at the location to form an image of the inconsistency at the location.

3. The scanning system of claim 1, wherein the translating structure is configured to move rotationally around the elongate structure when the scanner performs the second scan as a rotational scan using the x-ray beam in the second orientation.

4. The scanning system of claim 3, wherein the translating structure moves axially to return to the location after completing the axial scan of the elongate structure with the x-ray beam in the first orientation and moves rotationally at the location to perform the second scan as the rotational scan at the location using the x-ray beam in the second orientation.

5. The scanning system of claim 3, wherein the translating structure halts moving axially along a length of the elongate structure at the location and moves rotationally around the location to perform the second scan as the rotational scan using the x-ray beam in the second orientation.

6. The scanning system of claim 1, wherein the x-ray beam changes between the first orientation and the second orientation by rotating a collimator in the scanner.

7. The scanning system of claim 1, wherein the x-ray beam changes between the first orientation and the second orientation by changing dimensions of a slit in a collimator of the scanner.

8. The scanning system of claim 7, wherein the dimensions comprise a width for the slit and a height for the slit.

9. The scanning system of claim 1, wherein the translating structure is selected from one of a motorized arm, a crawler arm, and a track-based arm.

10. The scanning system of claim 1, wherein the scanner is comprised of at least one of an x-ray scanning system, a backscatter x-ray system, or a through transmission x-ray system.

11. The scanning system of claim 1, wherein the elongate structure is selected from one of a pipe, a drum, a conduit, a structural cable, a stringer, a structural beam, a wind turbine blade, a station, and a piling.

12. The scanning system of claim 1, wherein the inconsistency is selected from at least one of a corrosion, a crack, a spalling, a delamination, or a void.

13. A pipe scanning system comprising:
a translating structure configured to move axially and rotationally on a pipe;

a scanner connected to the translating structure, wherein the scanner is configured to scan an object utilizing an x-ray beam configured to have a first orientation and a second orientation that is substantially perpendicular to the first orientation; and a controller in communication with the translating structure and the scanner, wherein the controller controls the translating structure to move axially along the pipe while the scanner performs an axial scan of the pipe using the x-ray beam at the first orientation and move rotationally to perform a rotational scan of the pipe using the x-ray beam at the second orientation when an inconsistency is detected in the axial scan at a location on the pipe, and combines first data from the axial scan at the location with second data from the rotational scan at the location to form an image of the inconsistency at the location.

14. The pipe scanning system of claim 13, wherein the translating structure moves axially to return to the location after completing the axial scan of the pipe with the x-ray beam in the first orientation and moves rotationally at the location to perform the rotational scan at the location using the x-ray beam in the second orientation.

15. The pipe scanning system of claim 13, wherein the translating structure halts moving axially along a length of the pipe at the location and moves rotationally around the location to perform the rotational scan using the x-ray beam in the second orientation.

16. A method for scanning an elongate structure, the method comprising:
moving a scanner in a scanning system axially along the elongate structure using a translating structure in the scanning system;
scanning the elongate structure axially using an x-ray beam emitted by the scanner as the scanner moves axially along the elongate structure to perform an axial scan, wherein the x-ray beam has a first orientation;
detecting a location on the elongate structure having an inconsistency while scanning the elongate structure axially; and
scanning the elongate structure at the location with the x-ray beam in a second orientation to perform a second scan.

17. The method of claim 16 further comprising:
combining first data from the axial scan at the location with second data from a rotational scan at the location to form an image of the inconsistency at the location.

18. The method of claim 17 further comprising:
performing an action based on the image of the inconsistency.

19. The method of claim 16 further comprising:
moving the translating structure rotationally around the elongate structure when the scanner performs a second scan as a rotational scan using the x-ray beam in the second orientation.

20. The method of claim 19 further comprising:
moving the translating structure axially to return to the location after completing the axial scan of the elongate structure with the x-ray beam in the first orientation prior to moving the translational structure rotationally at the location to perform the second scan as the rotational scan at the location using the x-ray beam in the second orientation.

21. The method of claim 19 further comprising:
halting moving axially along a length of the elongate structure at the location prior to moving rotationally around the location to perform the second scan as the rotational scan is performed using the x-ray beam in the second orientation.

22. The method of claim 16 further comprising:
rotating a collimator in the scanner to change the x-ray beam between the first orientation and the second orientation.

23. The method of claim 16 further comprising:
changing dimensions of a slit in a collimator of the scanner to change the x-ray beam between the first orientation and the second orientation.

24. The method of claim 23, wherein the dimensions comprise a width for the slit and a height for the slit.

25. The method of claim 16, wherein the translating structure is selected from one of a motorized arm, a crawler arm, and a track-based arm.

26. The method of claim 16, wherein the scanner is comprised of at least one of an x-ray scanning system, a backscatter x-ray system, or a through transmission x-ray system.

27. The method of claim 16, wherein the elongate structure is selected from one of a pipe, a drum, a conduit, a structural cable, a stringer, a structural beam, a wind turbine blade, a station, and a piling.

28. The method of claim 16, wherein the inconsistency is selected from at least one of a corrosion, a crack, a spalling, a delamination, or a void.

\* \* \* \* \*